US005843334A

United States Patent [19]

Saheki et al.

[11] Patent Number: 5,843,334

[45] Date of Patent: Dec. 1, 1998

[54] METHOD OF PRODUCING EMULSIONS AND AN EMULSIFICATION APPARATUS

[75] Inventors: Akira Saheki, Nagaokakyo; Junzo Seki, Ibaraki, both of Japan

[73] Assignee: Nippon Shinyaku Co., Ltd., Kyoto, Japan

[21] Appl. No.: 765,486

[22] PCT Filed: Jun. 19, 1995

[86] PCT No.: PCT/JP95/01209

§ 371 Date: Dec. 13, 1996

§ 102(e) Date: Dec. 13, 1996

[87] PCT Pub. No.: WO95/35157

PCT Pub. Date: Dec. 28, 1995

[30] Foreign Application Priority Data

Jun. 20, 1994 [JP] Japan .................................... 6-137054

[51] Int. Cl.[6] ............................ B01J 13/00; A61K 9/127; B01F 5/06; B01F 15/02

[52] U.S. Cl. ........................... 252/314; 252/312; 264/4.1; 366/192; 366/176.1; 424/450; 425/5; 514/941

[58] Field of Search .................................... 252/312, 314; 424/450; 425/5; 366/192, 176.1; 514/941; 264/4.1

[56] References Cited

U.S. PATENT DOCUMENTS

| | | | |
|---|---|---|---|
| 1,817,958 | 8/1931 | Zwilgmeyer | 252/314 X |
| 3,684,251 | 8/1972 | Bowling | 252/314 X |
| 4,057,223 | 11/1977 | Rosenberger | 366/172 |
| 4,081,863 | 3/1978 | Rees | 366/192 X |
| 4,344,752 | 8/1982 | Gallagher, Jr. | 366/150 X |
| 4,383,769 | 5/1983 | Pandolfe | 366/337 |
| 4,608,211 | 8/1986 | Handjani et al. | 424/450 X |
| 4,621,023 | 11/1986 | Redziniak et al. | 252/314 X |
| 4,664,528 | 5/1987 | Rodgers et al. | 366/142 |
| 5,149,720 | 9/1992 | DesMarais et al. | 521/63 |
| 5,152,923 | 10/1992 | Weder et al. | 252/314 X |
| 5,173,007 | 12/1992 | Krajieck | 252/314 X |
| 5,453,447 | 9/1995 | End et al. | 424/450 X |
| 5,554,382 | 9/1996 | Castor | 424/450 |

FOREIGN PATENT DOCUMENTS

| | | | |
|---|---|---|---|
| 0 568 070 A1 | 4/1993 | European Pat. Off. . | |
| 55-77035 | 6/1980 | Japan . | |
| 59-026128 | 2/1984 | Japan | B01F 5/00 |
| 62-001444 | 1/1987 | Japan | B01F 3/08 |
| 2 036 534 | 11/1979 | United Kingdom . | |

OTHER PUBLICATIONS

Abstract of Japanese 55077035.
Derwent Abstract of Japanese 59026128.
Derwent Abstract of Japanese 62001444.

*Primary Examiner*—Richard D. Lovering
*Attorney, Agent, or Firm*—Graham & James LLP

[57] ABSTRACT

There is provided a method of producing an emulsion by which an emulsion consisting of uniform and microfine globules can be easily obtained with a reduced energy input as compared with the conventional technology.

This method of producing an emulsion comprises applying a back pressure equal to not less than 0.2% but less than 5% of the pressure acting on the point of high-pressure emulsifying action in a high-pressure emulsification zone in the course of production of an emulsion with a high-pressure emulsification equipment. The back pressure can be obtained typically by equipping an emulsification machine with a pipeline smaller in inside diameter than the discharge line of the machine.

10 Claims, 3 Drawing Sheets

METHOD OF PRODUCING EMULSIONS AND AN EMULSIFICATION APPARATUS

This application is filed under 35 USC §371 from PCT/JP95/01209, filed Jun. 19 1995 based on Japanese patent application 6/137054, filed 20 Jun., 1994.

TECHNICAL FIELD

The present invention relates to a method of producing an emulsion using a high-pressure emulsification equipment. More particularly, the invention relates to a method of producing an emulsion characterized by applying a back pressure equal to not less than 0.2% but less than 5% of the pressure acting on the point of high-pressure emulsifying action in a high-pressure emulsification zone in the course of production of an emulsion with a high-pressure emulsification equipment.

BACKGROUND TECHNOLOGY

In the pharmaceutical field, a great deal of research has been undertaken in recent years into a variety of performance dosage forms known as drug delivery systems (DDS).

One of such DDSs is an emulsion which consists of microglobular particles or droplets. Microglobules not exceeding 100 nm in particle diameter are scarsely taken up in the biological tissues with a well-developed reticuloendothelial system (RES), such as the liver and the spleen, and may selectively permeate into the diseased tissues with enhanced vascular permeability. Therefore, any drug included in such a microglobule may find its way efficiently to the target lesion and emulsions consisting of drug-containing microglobules are of great use as antitumor drugs, antiinflammatory drugs, antiviral drugs, analgesics, antiallergic drugs, antiulcer drugs, and chemotherapeutic drugs, among others (Japanese Kokai Tokkyo Koho (JP Kokai) H2-203 and H3-176425, WO91/07973, WO91/07962, WO91/07964, WO91/10431, etc.). On the other hand, emulsion particles larger than 100 nm in diameter are more readily taken up in tissues with developed RES and, therefore, emulsions consisting of globules with a mean particle diameter of about 200 nm have been used clinically as, for example, infusions for hyperalimentation or nutritional supplementation [SAISHIN IGAKU, 40, 1806-1813 (1980)].

An emulsion is generally produced by using a high-pressure emulsification equipment for efficient breaking-up, dispersing, and emulsification.

The conventional high-pressure emulsification equipment is available either in the type which does not involve application of a pressure (back pressure) in a direction reverse to the direction of flow of the emulsion fluid at the outlet of the equipment or the type which involves application of a back pressure equal to about 20–25% of the pressure acting on the point of high-pressure emulsifying action in the high-pressure emulsification zone. Although emulsions can be produced by using such emulsification equipment, a great deal of energy is required for applying a high pressure to the point of emulsifying action in the high-pressure emulsification zone or for causing the emulsion fluid to traverse the point of emulsifying action repeatedly to produce an emulsion consisting of microglobular particles with diameters in the range of tens through hundreds of nanometers. In addition, it is difficult to obtain microglobules uniform in particle diameter. Thus, the conventional high-pressure emulsification equipment is not necessarily a satisfactory equipment. In particular, it is difficult to produce an emulsion consisting of microglobules (a mean particle diameter not greater than 70 nm) by using the conventional high-pressure emulsification equipment.

SUMMARY OF THE INVENTION

The present invention has for its object to provide a method of producing an emulsion consisting of uniform and microfine globules with a reduced energy input (a shorter treatment time or a lower pressure) with ease.

After much research the inventors of the present invention discovered by chance that the above-mentioned object can be accomplished by the simple procedure of applying a back pressure equal to not less than 0.2% but less than 5% of the pressure acting on the point of high-pressure emulsifying action in a high-pressure em ulsification zone (hereinafter referred to as processing pressure) in the course of production of an emulsion with a high-pressure emulsification equipment. The present invention has been developed on the basis of the above finding.

BRIEF DESCRIPTION OF THE DRAWINGS

FIGS. 2-1 to 2-5 are schematic views of devices for applying back pressure to the high-pressure emulsification zone in a high-pressure emulsification apparatus;

FIG. 3 is a graph showing particle size distribution of emulsions obtained using the present invention (open circles) and the prior art (closed circles);

FIG. 4 is a graph showing the relationship between particle diameter and back pressure.

The present invention is essentially focused on the back pressure applied to the outlet region of a high-pressure emulsification equipment.

The present invention is now described in detail.

Figure 1:
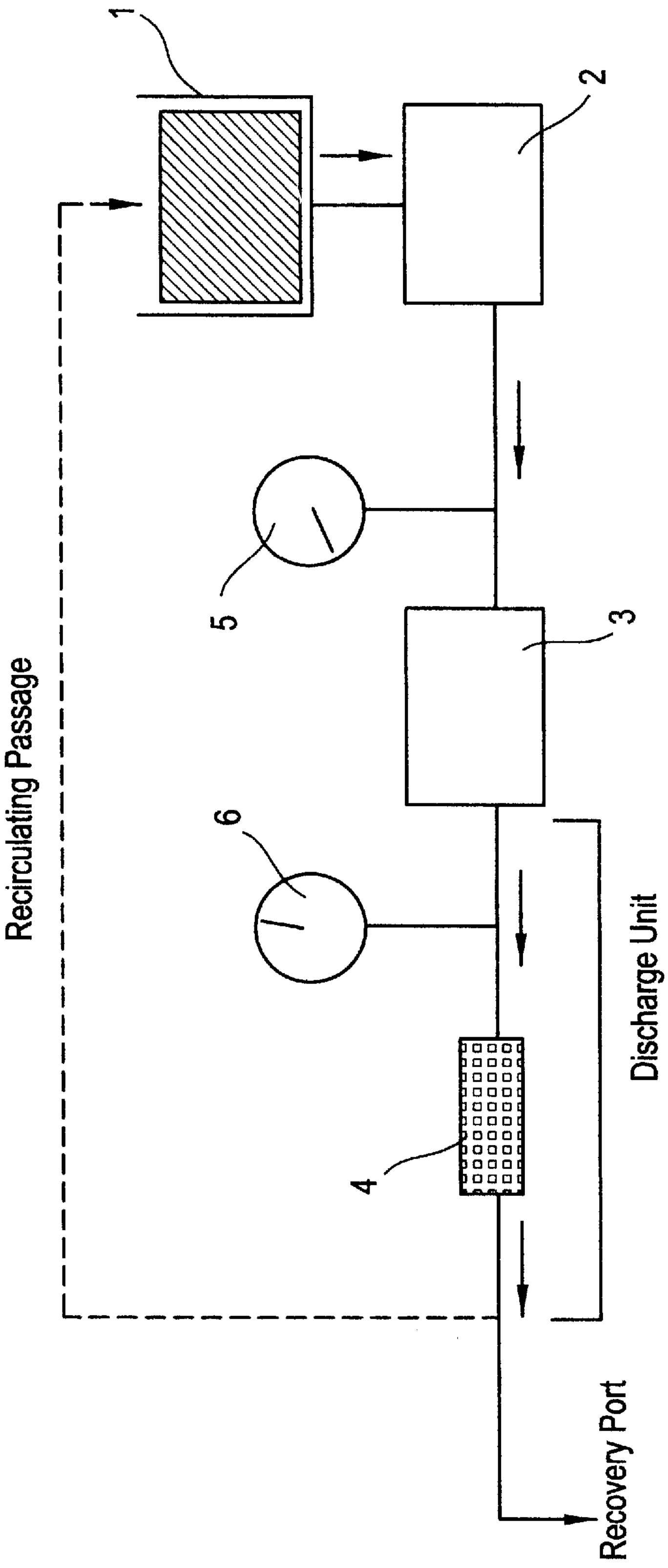
FIG. 1 is a schematic view of a general high-pressure emulsification apparatus according to the invention.
Figure 2A:
Figure 2B:
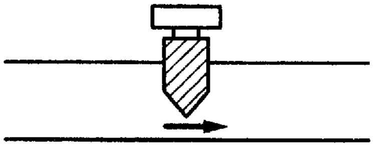
Figure 2C:
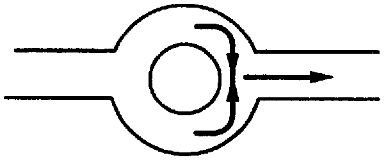
Figure 2D:
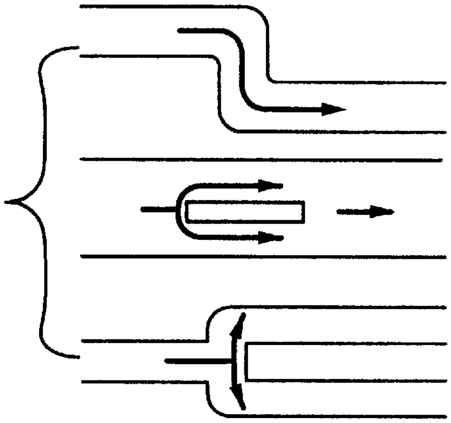
Figure 2E:
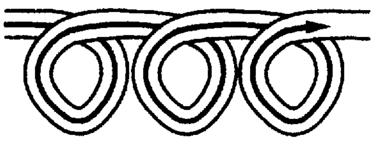

Referring to FIG. 1 of the drawings, the arrow indicates the direction of flow of the mixture of emulsion or liposome components. The reference numeral 1 represents a feed stock supply tank, 2 a pump, 3 a high-pressure emulsification zone, 4 a back pressure device, 5 a pressure meter for measuring the pressure acting on the point of high-pressure emulsifying action in the high-pressure emulsification zone, and 6 a pressure meter for measuring the back pressure. The back pressure device may be any of the devices shown in FIGS. 2-1 to 2-5, where the arrow indicates the direction of flow of the mixture of emulsion or liposome components and region where the back pressure is generated.

Figure 3:
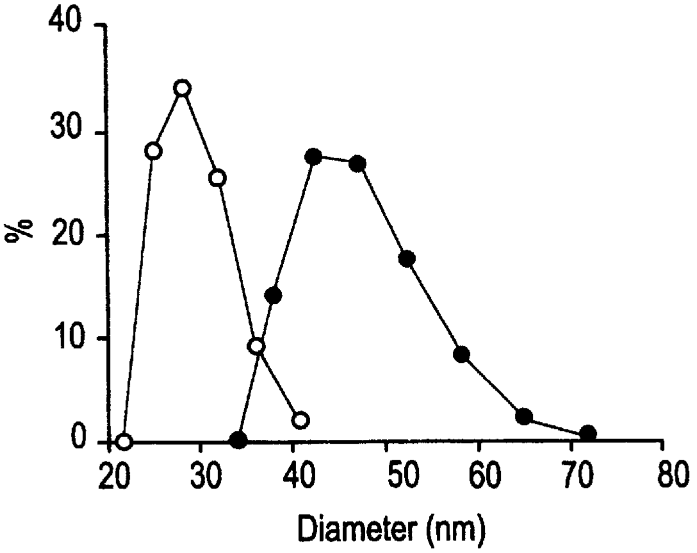

FIG. 3 shows particle size distributions obtained with and without the use of the invention. The open circles represent the particle size distribution of the emulsion produced in Example 4 using the method of the invention, and the closed circles represent the particle size distribution of the emulsion produced in Comparative Example 3 by following the prior art. The ordinate represents distribution rate (%) and the abscissa represents particle diameter (nm).

Figure 4:
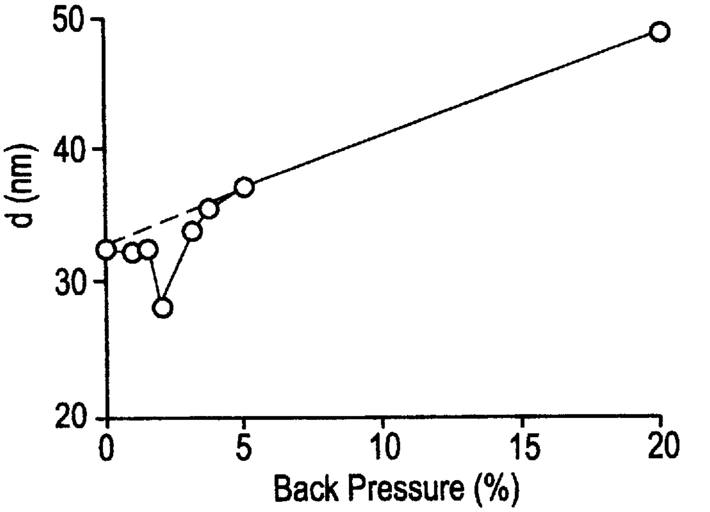

FIG. 4 shows the relationship of back pressure to mean particle diameter. The abscissa represents back pressure (% of processing pressure) and the ordinate represents mean particle diameter (nm).

The present invention can be carried into practice by using a high-pressure emulsification apparatus which is available upon providing a conventional high-pressure emulsification machine with a device capable of applying a back pressure to the outlet of the machine (cf. FIG. 1).

The conventional high-pressure emulsification machine that can be utilized includes but is not limited to liquid-liquid collision type high-pressure emulsification equipment [e.g. Microfluidizer (tradename; manufactured by Microfluidics Co.), Nanomizer (tradename; manufactured by Nanomizer Co.), Ultimaizer (tradename; manufactured by Tau Technology), etc.], and high-pressure homogenizers such as Mant on-Gaulin homogenizer.

The back pressure can be obtained by applying a load against the flow of the emulsion fluid at the outlet of the equipment. The load can be applied in the following and other schemas.

(1) The emulsion fluid is guided from a large-diameter line to a small-diameter line.

(2) Droplets of the emulsion fluid are caused to impinge against each other.

(3) The emulsion fluid is caused to bump against the wall of the piping or the like.

(4) A helical flow is created in the emulsion fluid.

The device for applying a back pressure can be a device implementing any of the above schemas or a device representing a combination of two or more of the above schemas. Specifically, a system equipped with a piping having an inside diameter smaller than that of the discharge line of a high-pressure emulsification machine (cf. FIG. 2-1), a system equipped with a control valve capable of constricting the passageway of the emulsion fluid (cf. FIG. 2-2), a system comprising a branching and terminally converging line (cf. FIG. 2-3), a system comprising a line configured like the letter Z, the inverted letter Y, or the letter T (cf. FIG. 2-4), and a system having a long coil-shaped pipeline (cf. FIG. 2-5). The kind of material that can be used for the construction of the main part (where the emulsion components flow) of such equipment is not restricted only if it is resistant to the back pressure and resists corrosion, too, thus including stainless steel, glass, sintered diamond, and ceramic, among others.

The above-mentioned device capable of applying a back pressure can be directly connected to the outlet of a high-pressure emulsification machine or jointed to the discharge line by welding or through a pressure-resistant coupling.

The magnitude of said back pressure need only be in the range of not less than 0.2% and less than 5% of the processing pressure but is preferably 0.94–3.75%. A back pressure equivalent to 2% is still more preferred. If the back pressure is less than 0.2%, no sufficient effect will be obtained. If the back pressure is 5% or higher, a rather adverse effect will be encountered. Thus, the emulsion consisting of desired microglobules will not be obtained even by prolonged processing. Though there is virtually no limitation on the magnitude of the processing pressure, it should be not less than 4,300 psi, preferably 7,300–29,100 psi, and, for still better results, 10,000–22,000 psi.

Any high-pressure emulsification machine equipped with a device capable of applying a back pressure within the above-mentioned range at the outlet also falls within the scope of the present invention.

Except for applying a back pressure equal to not less than 0.2% but less than 5% of the processing pressure, the method of the present invention is not different from the conventional technology and except for provision of a device for applying a back pressure at the outlet, the emulsification apparatus of the present invention is not different from the conventional high-pressure emulsification equipment. Therefore, production of an emulsion according to the present invention can be carried out in otherwise the same manner as the conventional technology using a high-pressure emulsification equipment. By way of example, a crude emulsion prepared from emulsion components and water by means of a homogenizer or the like can be emulsified in the manner specific to the mechanism of the emulsification machine used.

Therefore, there is no particular limitation on the emulsion that can be produced by the method and emulsification apparatus of the present invention. As examples of such emulsion, there can be mentioned those described in JP Kokai H2-203, JP Kokai H3-176425, WO91/07973, WO91/07962, WO91/07964, WO91/10431, JP Kokai S58-222014, JP Kokai S62-29511, and JP Kohyo S63-500456, among others. To be specific, there can be mentioned an emulsion of microglobules essentially comprising a simple lipid (e.g. the simple lipid and triolein derived from purified soybean oil) as the principal component of an internal phase and a surfactant (e.g. the phospholipid derived from egg yolk or soybean) as the principal component of an external phase, said internal phase accounting for 0.1–50% (w/v) and said external phase accounting for 0.01–40% (w/v) of the whole emulsion. In this connection, liposomal preparations as described in *Liposomes* (Nanko-do, 1988) can also be manufactured by the method (emulsification equipment) of the present invention. By the method (emulsification equipment) of the present invention, both an emulsion containing a medicinally active substance in each microglobule and an emulsion not containing a medicinally active substance can be manufactured.

The method of the present invention is particularly suited for the manufacture of a non-liposomal emulsion consisting of microglobular particles with a mean particle diameter of 5 nm–100 nm and especially suitable for the manufacture of a non-liposomal emulsion consisting of microglobular particles with a mean particle diameter of 10 nm–50 nm. Furthermore, the method of the present invention is suited for the manufacture of an emulsion consisting of microglobules comprising a simple lipid, such as the simple lipid and triolein derived from purified soybean oil as the principal component of an internal phase and a surfactant, such as lecithin (phospholipid) derived from egg yolk, as the principal component of an external phase and having a mean particle diameter of 5 nm–100 nm. The method is still more suited for the manufacture of an emulsion consisting of microglobules composed of a simple lipid, such as the simple lipid and triolein derived from purified soybean oil, as the principal component of an internal phase and a surfactant, such as lecithin (phospholipid) derived from egg yolk, as the principal component of an external phase and having a mean particle diameter of 10 nm–50 nm. The method is especially suited for the manufacture of an emulsion consisting of microglobules with a mean particle diameter of not greater than 40 nm.

The particle diameter and morphology of the emulsion globules obtainable by the method of the present invention can be easily ascertained by electron microscopy or using a light-scattering particle size analyzer.

EFFECTS OF THE INVENTION (1) In accordance with the present invention, an emulsion made up of microglobules can be produced with a smaller energy input than heretofore required. Thus, the emulsion can be produced in a shorter time compared with the usual production time. By way of illustration, the dispersing and emulsifying process which required 80 minutes in the past can now be achieved in 40 minutes, assuming that the energy input is fixed (cf. Test Example 1). Furthermore, because an emulsion of microglobules can thus be produced with a lower energy input, contamination with foreign matter derived form the seals of the high-pressure emulsification equipment or the parts constituting the high-pressure emulsification zone can be minimized and, in addition, degradation of emulsion components due to temperature rises during high-pressure emulsification can be held to the minimum, with the result that an emulsion of higher quality compared with the conventional emulsion can be obtained. Furthermore, a large-scale high-energy emulsification hardware is not essential.

(2) In accordance with the present invention, an emulsion of microglobules with a uniform and narrower particle size distribution as compared with the conventional emulsion can be easily produced.

(3) In accordance with the present invention, an emulsion made up of ultrafine particles which cannot be obtained by the prior technology can be produced.

BEST MODE OF PRACTICING THE INVENTION

The following working examples and test examples are intended to describe the present invention in further detail. The particle size distribution and particle diameter were measured with the light-scattering particle size analyzer (DLS-700) available from Otsuka Electronics Co., Ltd. and the mean particle diameter (d) was determined by the cumulant method.

Example 1

To 5 g of liquid paraffin and 5 g of Tween 80/Span 80 (HLB=10) was added 50 ml of purified water and the mixture was dispersed by a homogenizer to give a crude emulsion. This crude emulsion was further diluted with purified water to make 100 ml for use as a crude dispersion. This crude dispersion was emulsified by means of Microfluidizer (tradename, Microfluidics Co.; M110-E/H, the same applies hereinafter) at a processing pressure of 16,000 psi and a back pressure of 80 psi (0.5% of processing pressure) for 60 minutes to provide an emulsion. The resulting emulsion was composed of emulsion particles with a mean particle diameter of 30 nm.

The back pressure of 80 psi was obtained by attaching a coil of stainless steel piping measuring 5 m long and 6.35 mm in inside diameter to the outlet of the Microfluidizer used (cf. FIG. 2-5).

Example 2

To 100 g of purified soybean oil and 12 g of purified egg yolk lecithin was added 500 ml of purified water and the mixture was dispersed by a homogenizer to give a crude emulsion. This crude emulsion was diluted with a further amount of purified water to make 1 liter. This crude dispersion was done one cycle treatment (passed once) by means of the Microfluidizer set to a processing pressure of 7,300 psi and a back pressure of 365 psi (5% of processing pressure) to provide an emulsion. The resulting emulsion was composed of globules with a mean particle diameter of 200 nm.

The back pressure of 365 psi was obtained by attaching a coil of stainless steel piping measuring 28.5 m long and 6.35 mm in inside diameter to the outlet of the Microfluidizer used (cf. FIG. 2-5).

Example 3

To 5 g of purified soybean oil and 5 g of purified egg yolk lecithin was added 50 ml of water containing 2.21 g of glycerin and the mixture was dispersed by a homogenizer to give a crude emulsion. This crude emulsion was further diluted with purified water to make 100 ml for use as a crude dispersion. This crude dispersion was emulsified under water-cooling by means of the Microfluidizer at a processing pressure of 16,000 psi and a back pressure of 320 psi (2% of processing pressure) for 20–90 minutes to provide an emulsion.

The back pressure of 320 psi was obtained by attaching a device comprising a pressure-regulating needle valve (cf. FIG. 2-2) to the outlet of the Microfluidizer used.

Example 4

To 5 g of purified soybean oil and 5 g of purified egg yolk lecithin was added 50 ml of water containing 10 g of maltose and the mixture was dispersed by a homogenizer to give a crude emulsion. This crude emulsion was further diluted with purified water to make 100 ml for use as a crude dispersion. This crude dispersion was emulsified under water-cooling by means of Microfluidizer at a processing pressure of 16,000 psi and a back pressure of 320 psi (2% of processing pressure) for 90 minutes to provide an emulsion. The resulting emulsion was composed of microglobules with a mean particle diameter of 28 nm.

The back pressure of 320 psi was obtained by attaching a device comprising a pressure-regulating needle valve (cf. FIG. 2-2) to the outlet of the Microfluidizer used.

Example 5

To 10 g of purified soybean oil and 10 g of purified egg yolk lecithin was added 100 ml of water containing 10 g of maltose and the mixture was dispersed by a homogenizer to give a crude emulsion. This crude emulsion was further diluted with purified water to make 200 ml for use as a crude dispersion. This crude dispersion was emulsified under water-cooling by means of Microfluidizer at a processing pressure of 25,500 psi and a back pressure of 510 psi (2% of processing pressure) for 40 minutes to provide an emulsion. The resulting emulsion was composed of microglobules with a mean particle diameter of 30 nm.

The back pressure of 510 psi was obtained by attaching a device comprising a pressure-regulating needle valve (cf. FIG. 2-2) to the outlet of the Microfluidizer used.

Example 6

To 40 g of purified soybean oil and 40 g of purified egg yolk lecithin was added 19 ml of water containing 10 g of maltose and the mixture was dispersed by a homogenizer to give a crude emulsion. This crude emulsion was further diluted with purified water to make 100 ml for use as a crude dispersion. This crude dispersion was emulsified under water-cooling by means of Microfluidizer at a processing pressure of 16,000 psi and a back pressure of 320 psi (2% of processing pressure) for 45 minutes to provide an emulsion. The resulting emulsion was composed of microglobules with a mean particle diameter of 40 nm.

The back pressure of 320 psi was obtained by attaching a device comprising a pressure-regulating needle valve (cf. FIG. 2-2) to the outlet of the Microfluidizer used.

Example 7

To 20 g of purified soybean oil and 20 g of purified egg yolk lecithin was added 50 ml of water containing 10 g of maltose and the mixture was dispersed by a homogenizer to give a crude emulsion. This crude emulsion was further diluted with purified water to make 100 ml for use as a crude dispersion. This crude dispersion was emulsified under water-cooling by means of Microfluidizer at a processing pressure of 16,000 psi and a back pressure of 320 psi (2% of processing pressure) for 45 minutes to provide an emulsion. The resulting emulsion was composed of microglobules with a mean particle diameter of 40 nm.

The back pressure of 320 psi was obtained by attaching a device comprising a pressure-regulating needle valve (cf. FIG. 2-2) to the outlet of the Microfluidizer used.

Comparative Example 1

The same crude dispersion as described in Example 3 was emulsified with the Microfluidizer set to a processing pressure of 16,000 psi and a back pressure of 0 psi (0% of processing pressure) under water-cooling for 20–90 minutes to provide an emulsion.

Comparative Example 2

The same crude dispersion as described in Example 3 was emulsified with the Microfluidizer set to a processing pressure of 16,000 psi and a back pressure of 3,200 psi (20% of processing pressure) under water-cooling for 20–90 minutes to provide an emulsion Comparative Example 3

The same crude dispersion as described in Example 4 was emulsified with the Microfluidizer set to a processing pressure of 16,000 psi and a back pressure of 3,200 psi (20% of processing pressure) under water-cooling for 90 minutes to provide an emulsion.

Test Example 1

For the emulsions produced in Example 3 (method of the invention) and Comparative Examples 1 and 2 (controls), the particle diameter of constituent particles was measured. The results are presented in Table 1.

TABLE 1

| Emulsification time | Example 3 | Comparative Example 1 | Comparative Example 2 |
|---|---|---|---|
| 20 min. | 57 nm | 75 nm | 105 nm |
| 40 min. | 41 nm | 54 nm | 85 nm |
| 60 min. | 32 nm | 49 nm | 73 nm |
| 80 min. | 31 nm | 42 nm | 69 nm |
| 90 min. | 28 nm | 42 nm | 69 nm |

It will be apparent from Table 1 that emulsions of microglobular particles are obtained in a shorter time in accordance with the present invention as compared with the control methods and that emulsions of microglobules with a mean particle diameter of 30 nm which cannot be obtained by the control methods can be successfully obtained by the method of the present invention.

Test Example 2

For the emulsions produced in Example 4 (method of the invention) and Comparative Examples 3 (controls), the particle diameter of constituent particles was measured. It will be apparent from FIG. 3 that the particle size distribution according to the present invention is shifted downward on the diameter scale as compared with the control distribution. Moreover, the width of particle size distribution at half height according to the invention is 11 nm, being smaller than 18 nm for the control and, therefore, the method of the invention shows a narrower particle size distribution (satisfactory uniformity) than the control.

Test Example 3

The crude dispersion as used in Example 4 was emulsified under water-cooling with the Microfluidizer set to a processing pressure of 16,000 psi and a varying back pressure of 0 psi, 150 psi, 250 psi, 320 psi, 500 psi, 600 psi, 800 psi, or 3,200 psi (0%, 0.94%, 1.56%, 2.00%, 3.13%, 3.75%, 5%, or 20% of processing pressure) for 90 minutes to provide an emulsion.

The back pressures mentioned above were applied by adjusting a device having a pressure-regulating needle valve (FIG. 2-2) as connected to the outlet of the Microfluidizer used.

It will be apparent from FIG. 4 that while a substantial linearity is obtained upon plotting the 3 points of 0%, 5%, and 20%, actually a considerable deviation from linearity occurred in the range of 0–5%, giving emulsions of microglobules with mean particle diameters smaller than the mean particle diameter deduced from the above-mentioned linear relationship. This is a very singular finding.

What is claimed is:

1. In a method of producing an emulsion or liposome in which the materials that will form the emulsion or liposome are subjected to high pressure as they flow in a first direction through a high-pressure emulsification zone to thus form the resultant emulsion or liposome, the improvement which comprises applying a back pressure to said high-pressure emulsification zone in a direction reverse to said first direction in an amount of not less than 0.2%, but less than 5%, of said high pressure in said emulsification zone.

2. The method according to claim 1, wherein the emulsion or liposome is caused to exit said emulsification zone, and said back pressure is applied to said emulsion or liposome at said exit.

3. The method according to claim 2, wherein said emulsion or liposome consists of microglobules with a mean particle diameter of 5 nm–100 nm.

4. The method according to claim 1, wherein said back pressure is about 2% of said high pressure in said high-pressure emulsification zone.

5. The method according to claim 1, wherein said emulsion or liposome consists of microglobules with a mean particle diameter of 5 nm–100 nm.

6. In a high-pressure emulsification apparatus, comprising a high-pressure emulsification zone, means for feeding emulsifiable or liposome-forming materials through said emulsification zone in a first direction and means for applying a high pressure to said materials as they flow through said emulsification zone, the improvement which comprises means capable of and adapted to apply a back pressure to said emulsification zone in a direction reverse to said first direction only in an amount between 0.2% and less than 5% of said high pressure in said emulsification zone, an outlet downstream of said emulsification zone through which said emulsion or liposome exits said apparatus and a passageway between said emulsification zone and said outlet.

7. Apparatus according to claim 6, wherein said back pressure applying means is at said outlet.

8. Apparatus according to claim 7, wherein said back pressure applying means comprises means for applying a back pressure in an amount of about 2% of the pressure in said emulsification zone.

9. Apparatus according to claim 8, wherein said back pressure applying means is piping smaller in inside diameter than said outlet, a regulating valve in said passageway and being only operable to constrict said passageway to provide a back pressure of 2%, a branched and terminally converging piping, piping configured like the letter Z, the inverted letter Y or the letter T, or an elongated piping in the shape of a coil.

10. Apparatus according to claim 7, wherein said back pressure applying means is piping smaller in inside diameter than said outlet, a regulating valve in said passageway and being only operable to constrict said passageway to provide a back pressure within the range of between 0.2% and less than 5%, a branched and terminally converging piping, piping configured like the letter Z, the inverted letter Y or the letter T, or an elongated piping in the shape of a coil.

* * * * *